United States Patent
Kawano et al.

(10) Patent No.: US 8,529,460 B2
(45) Date of Patent: Sep. 10, 2013

(54) MEASURING APPARATUS

(75) Inventors: Katsunori Kawano, Kanagawa (JP); Yoshio Nishihara, Kanagawa (JP); Yasuaki Kuwata, Kanagawa (JP)

(73) Assignee: Fuji Xerox Co., Ltd., Tokyo (JP)

(*) Notice: Subject to any disclaimer, the term of this patent is extended or adjusted under 35 U.S.C. 154(b) by 1189 days.

(21) Appl. No.: 12/421,000

(22) Filed: Apr. 9, 2009

(65) Prior Publication Data

US 2010/0069727 A1    Mar. 18, 2010

(30) Foreign Application Priority Data

Sep. 18, 2008    (JP) ................................ 2008-239444

(51) Int. Cl.
*A61B 5/02*    (2006.01)
*G01P 3/36*    (2006.01)

(52) U.S. Cl.
USPC ............................. 600/504; 356/27; 356/28.5

(58) Field of Classification Search
USPC .................................. 600/508; 356/27–28.5
See application file for complete search history.

(56) References Cited

U.S. PATENT DOCUMENTS

2003/0142291 A1* 7/2003 Padmanabhan et al. ........ 356/39
2008/0304042 A1* 12/2008 Ueno ............................... 356/4.1

FOREIGN PATENT DOCUMENTS

JP    01-233371    9/1989
JP    10-009943    1/1998

\* cited by examiner

*Primary Examiner* — Navin Natnithithadha
*Assistant Examiner* — Eric Messersmith
(74) *Attorney, Agent, or Firm* — Fildes & Outland, P.C.

(57) ABSTRACT

Provided is a measuring apparatus including: a driving unit that outputs first and second driving signals each having an opposite phase; a first semiconductor laser device, driven by the first driving signal, that emits a first laser beam to an object to be measured; a second semiconductor laser device, disposed near the first device and driven by the second driving signal, that emits a second laser beam to the object; a first detection unit that detects a first electrical signal that corresponds to the intensity of the first laser beam modulated due to the self-coupling effect; a second detection unit that detects a second electrical signal that corresponds to the intensity of the second laser beam modulated due to the self-coupling effect; a calculation unit that calculates differences between the first and second electrical signals; and a measuring unit that measures a state change of the object from the difference.

7 Claims, 6 Drawing Sheets

Observed waveform

US 8,529,460 B2

MEASURING APPARATUS

CROSS-REFERENCE TO RELATED APPLICATION

This application is based on and claims priority under 35 USC 119 from Japanese Patent Application No. 2008-239444 filed Sep. 18, 2008.

BACKGROUND

1. Technical Field

The present invention relates to a measuring apparatus.

2. Related Art

Various types of measurement that use a semiconductor laser for measuring oscillation, distance, velocity or the like of an object to be measured are known.

Such measurements use the self-coupling effect of the laser. The self-coupling effect of the laser is an effect where returned light or reflected light of a laser beam is amplified in a laser medium, and as a result, the laser oscillation state is modulated. For a semiconductor laser with high gain, even if the returned light has an intensity of less than one hundredths that of an emitted laser light beam, the state of the returned light may be observed at a high signal to noise ratio (SNR).

When the returned light is subjected to frequency shifts due to the Doppler effect, or the position of reflection from the object to be measured is varied and is subjected to phase modulation, the oscillation state of the laser due to the self-coupling effect may vary in accordance with the changes. By analyzing the variations, the velocity or displacement of the object may be measured.

SUMMARY

An aspect of the present invention provides a measuring apparatus that includes: a driving unit that outputs a first driving signal and a second driving signal having a phase opposite to that of the first driving signal; a first semiconductor laser device, driven by the first driving signal, that emits a first laser light beam to an object to be measured; a second semiconductor laser device, disposed in proximity to the first semiconductor laser device and driven by the second driving signal, that emits a second laser light beam to the object to be measured; a first detection unit that detects a first electrical signal, the first electrical signal corresponding to the intensity of the first laser light beam modulated due to the self-coupling effect; a second detection unit that detects a second electrical signal, the second electrical signal corresponding to the intensity of the second laser light beam modulated due to the self-coupling effect; a calculation unit that calculates a difference between the first electrical signal and the second electrical signal; and a measuring unit that measures a change in the state of the object to be measured based on the calculated difference.

BRIEF DESCRIPTION OF THE DRAWINGS

Exemplary embodiments of the present invention will be described in detail based on the following figures, wherein.

DETAILED DESCRIPTION

Figure 9:
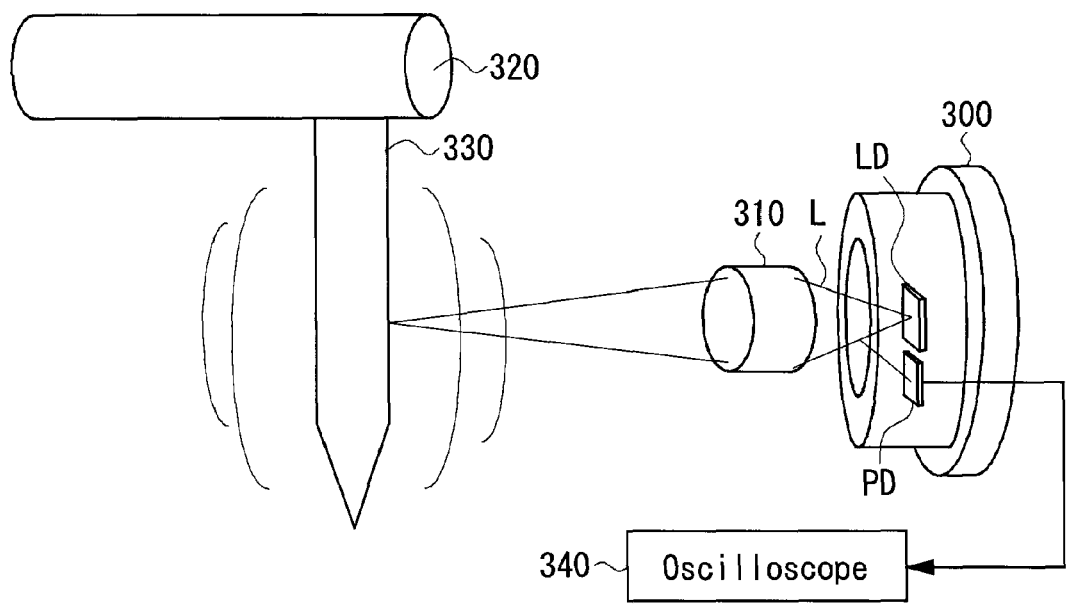
FIG. 9 illustrates an example of a configuration of a vibration measuring apparatus of a related art.

FIG. 9 illustrates an example of a general vibration measuring apparatus of a related art. As shown in FIG. 9, a laser apparatus 300 may include a laser device LD and a light receiving device (photo detector: PD.) The laser light beam L from the laser device LD through a lens 310 may irradiate a capillary 330 oscillated by an ultrasonic horn 320. Due to returned light reflected or scattered by the capillary 330, the oscillation state of the laser device LD may be modulated. The modulated oscillation state of the laser device LD may be monitored by the light receiving device PD.

Figure 10:
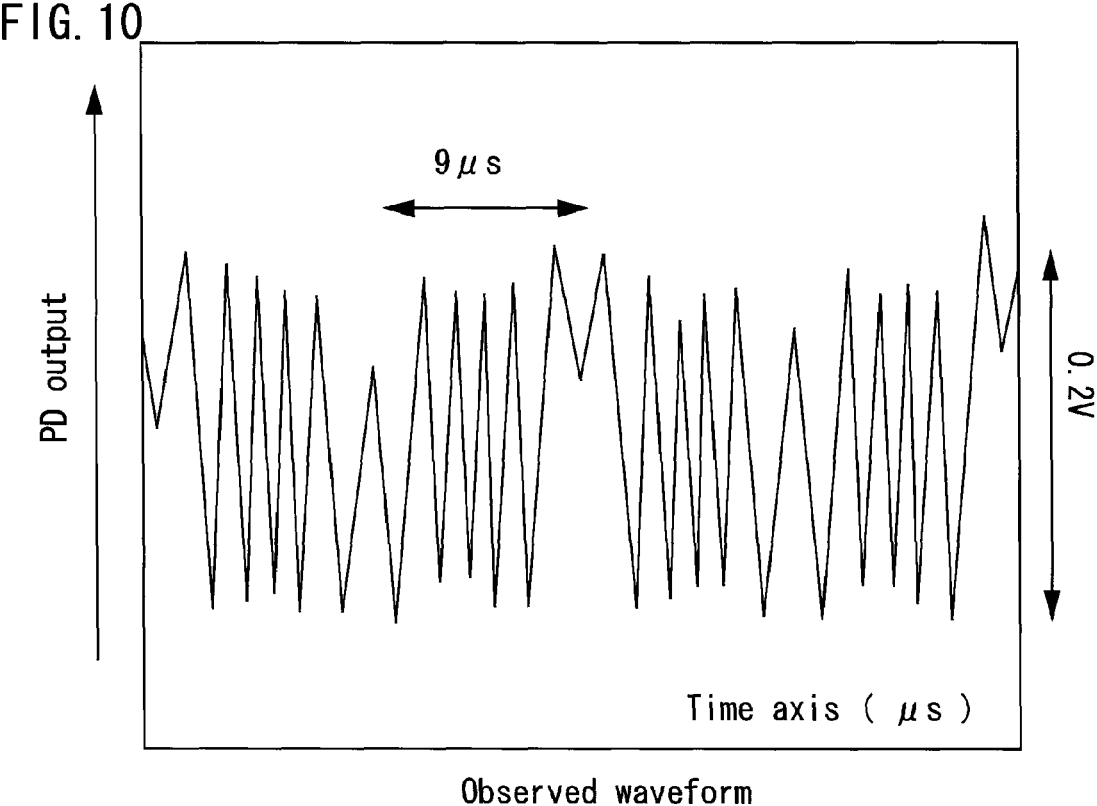
FIG. 10 illustrates an observed waveform of a vibration measuring apparatus of a related art.

FIG. 10 illustrates an observed waveform when the output signal of the light receiving device PD is coupled to an oscilloscope 340. The vertical axis shows output voltage (V) of the light receiving device, and the horizontal axis shows time (μs). As obvious from FIG. 10, in the output signal of the light receiving device PD, plural peaks having a short period are appeared in a range of about 0.2 V. These peaks mean that the laser oscillation state is modulated due to the returned light from the capillary 330, and beat signals are generated in the light intensity of the laser light beam.

If the intensity of a laser beam emitted to an object to be measured is $I_{in}$, the reflectivity of the object to be measured is r, and the self-coupling efficiency of the laser is α, then the intensity modulated due to the self-coupling effect becomes $I_{out}$ as expressed in Equation (4). Where Δω is the difference between the oscillation frequency when the laser light frequency is modulated during the measurement and the frequency of the returned light, Ω is the amount of phase-shift due to the Doppler effect upon the reflection from the object, Δd is the amount of displacement of the object to be measured, and k is the wave number vector of incident light.

$$I_{out}(t)=I_{in}+\Delta I(t)+r\alpha I_{in} \cos[(\Delta W+\Omega)t-k\Delta d] \quad (4)$$

As in Equation (4), when the object to be measured is subjected to the Doppler effect or displaced, the light intensity is oscillated as a function of cos.

Measuring apparatuses of related arts may measure changes in the state of an object to be measured, such as velocity or oscillation, by using Equation (4). However, if the reflectivity r of the object to be measured also varies, the detected light intensity $I_{out}$ is modulated due to the self-coupling effect, resulting that the measurement may provide an inaccurate result that includes noises.

In an exemplary embodiment of the present invention, two or more laser beams that are incoherent one another are used in proximity to each other to perform self-coupling of the laser beams. During the process, frequency modulation of the laser light beams is performed, and the modulation phases thereof are opposite each other. By obtaining a difference between signals by two self-coupling effects, noise components due to variations in the reflectivity of the object to be measured is removed, and changes in the state of the object to be measured, such as velocity, displacement or the like, may be measured. In a configuration of the present invention, two laser beams having a same property and in proximity to each other are emitted to the object to be measured, wherein, if a sufficient SNR is not obtained, it is preferable to use a lens such that the laser light beams are imaged onto the object to be measured. In contrast, in a case where a sufficient SNR is obtained, the lens is not necessary.

Examples described hereafter use a blood flow sensor that measures the velocity of hemoglobin in the blood as an example, and the velocity of an object to be measured such as hemoglobin, whose reflectivity of the surface to be irradiated readily varies, may be accurately measured.

Figure 1:
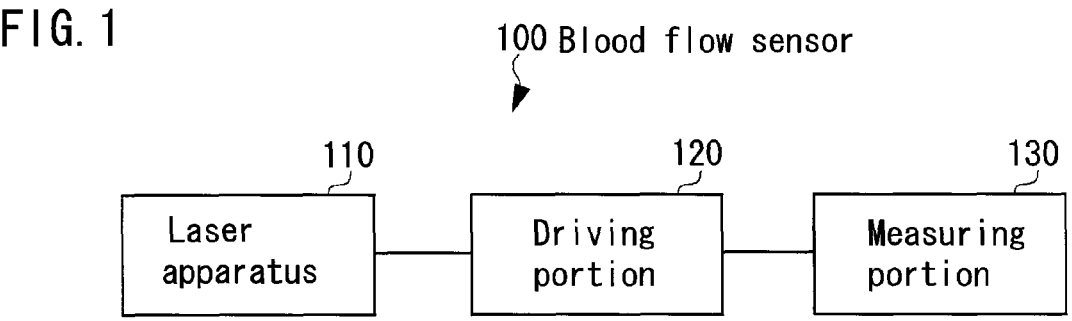
FIG. 1 is a block diagram illustrating a configuration of a blood flow sensor according to an aspect of the present invention.

FIG. 1 is a block diagram illustrating a configuration of a blood flow sensor according to an aspect of the present invention. A blood flow sensor 100 of the example may include a laser apparatus 110 having at least two semiconductor laser devices that emit coherent laser light, a driving portion 120 that drives each of the semiconductor laser devices, and a measuring portion 130 that measures changes in the state of an object to be measured from a signal obtained by use of the self-coupling effect.

The laser apparatus 110 of this example may preferably use a VCSEL as a semiconductor laser device. Two VCSELs, disposed on a same substrate as proximate as possible each other as long as their laser light beams do not interfere each other, are capable of emitting laser light beams each having a same property. By making two laser light beams proximate to each other, changes in the state of the object to be measured, which are in an approximately same condition, can be concurrently measured.

Figure 2:
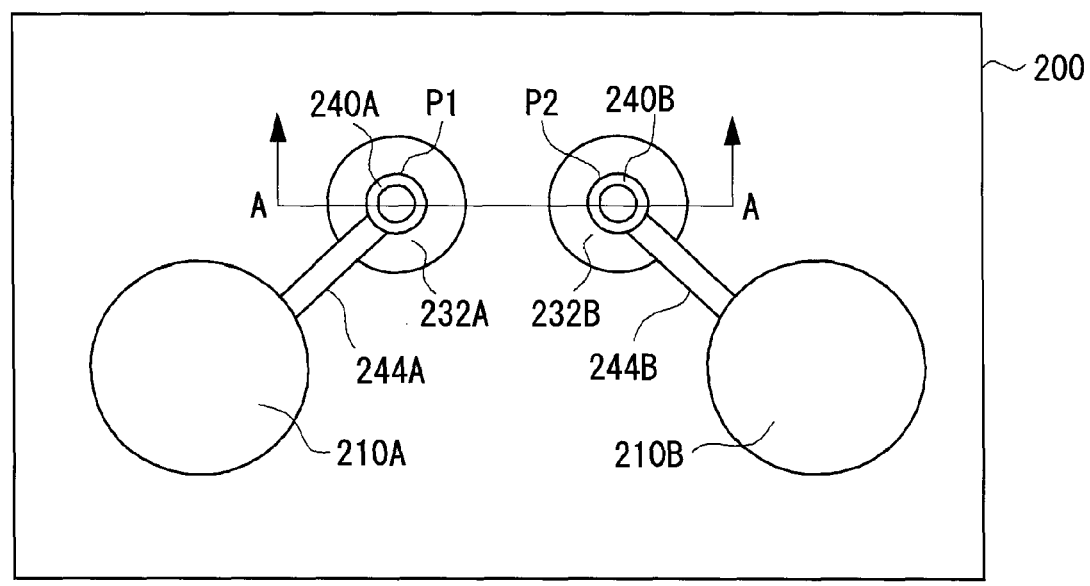
FIG. 2 is a plan view of VCSEL devices preferably used for a blood flow sensor of an example.
Figure 3:
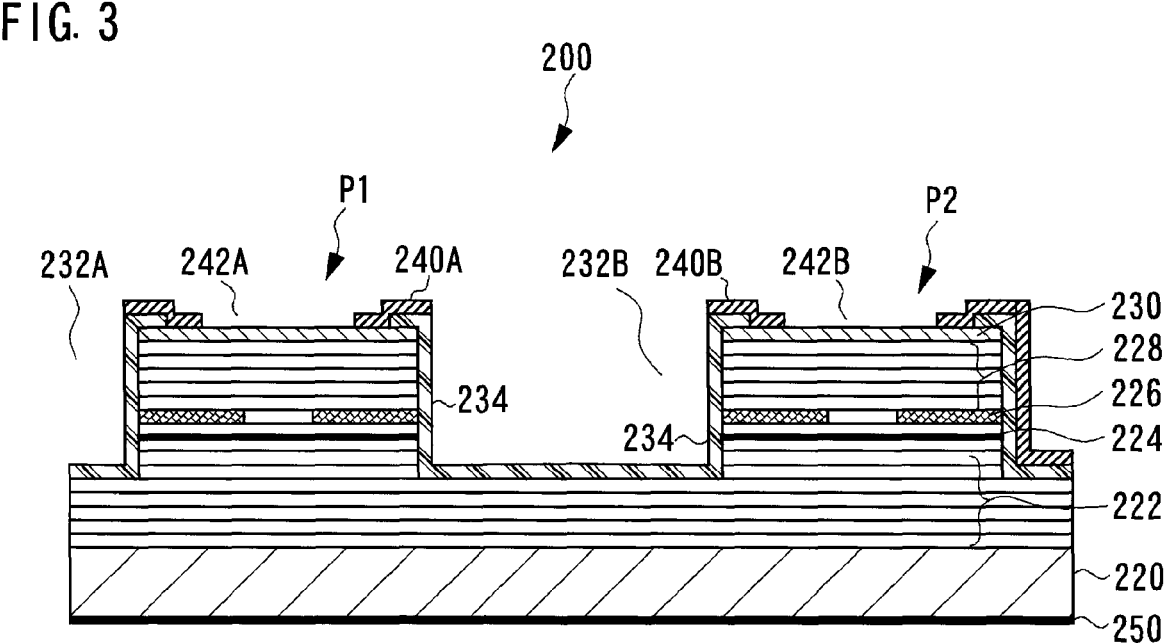
FIG. 3 is a cross sectional view taken along line A-A of FIG. 2.

FIG. 2 is a plan view of a semiconductor chip on which VCSELs are formed. FIG. 3 is a cross sectional view taken along line A-A of FIG. 2. As shown in FIG. 2, on a surface of a semiconductor chip 200, two posts (or mesas) P1 and P2 that become light emitting portions of laser light may be formed, and p-side electrodes 240A and 240B each formed at a top portion of the posts P1 and P2 may be coupled to electrode pads 210A and 210B by wirings 244A and 244B. The electrode pads 210A and 210B may be electrically coupled to the driving portion 120 by a coupling medium (not shown) such as a bonding wire.

As shown in FIG. 3, the semiconductor chip 200 may be formed on an n-type GaAs semiconductor substrate 220 by stacking semiconductor layers as follows: an n-type lower DBR 222 made by stacking plural AlGaAs layers each having a different Al-composition, an active region 224, a p-type AlAs current confining layer 226, a p-type upper DBR 228 made by stacking plural AlGaAs layers each having a different Al-composition, and a p-type GaAs contact layer 230. Semiconductor layers over the substrate 220 may be etched to form annular grooves 232A and 232B, and two cylindrical posts P1 and P2. An interlayer insulating film 234 may be formed to cover a bottom portion, a side portion, and a portion of the top portion of the posts P1 and P2. At a top portion of the posts P1 and P2, p-side electrodes 240A and 240B may be formed, which are electrically coupled to the contact layer 230 through a contact hole in the interlayer insulating film 234. At a center portion of the p-side electrodes 240A and 240B, emission windows 242A and 242B for emitting laser light may be formed. The p-side electrodes 240A and 240B may be coupled to the electrode pads 210A and 210B by the wirings 244A and 244B as shown in FIG. 2. On the back surface of the substrate 220, an n-side electrode 250 may be formed.

The lower DBR 222 is common to the posts P1 and P2, and the upper DBR 228 is electrically separated therefrom. In the posts P1 and P2, the lower DBR 222 and the upper DBR 228 may form a vertical resonator. When a first forward driving current is applied to the p-side electrode 240A and the n-side electrode 250, a laser light beam having a wavelength λ1 is emitted from the emission window 242A of the post P1 vertically with respect to the substrate. When a second forward driving current is applied to the p-side electrode 240B and the n-side electrode 250, a laser light beam having a wavelength λ2 is emitted from the emission window 242B of the post P2. The wavelengths λ1 and λ2 of the laser light beams emitted from posts P1 and P2 are slightly different from each other due to the amount of the driving current. As such, by monolithically forming VCSELs on a semiconductor laser chip, coherent laser light beams each having a same property and do not interfere one another can be provided in proximate to each other.

Figure 4:
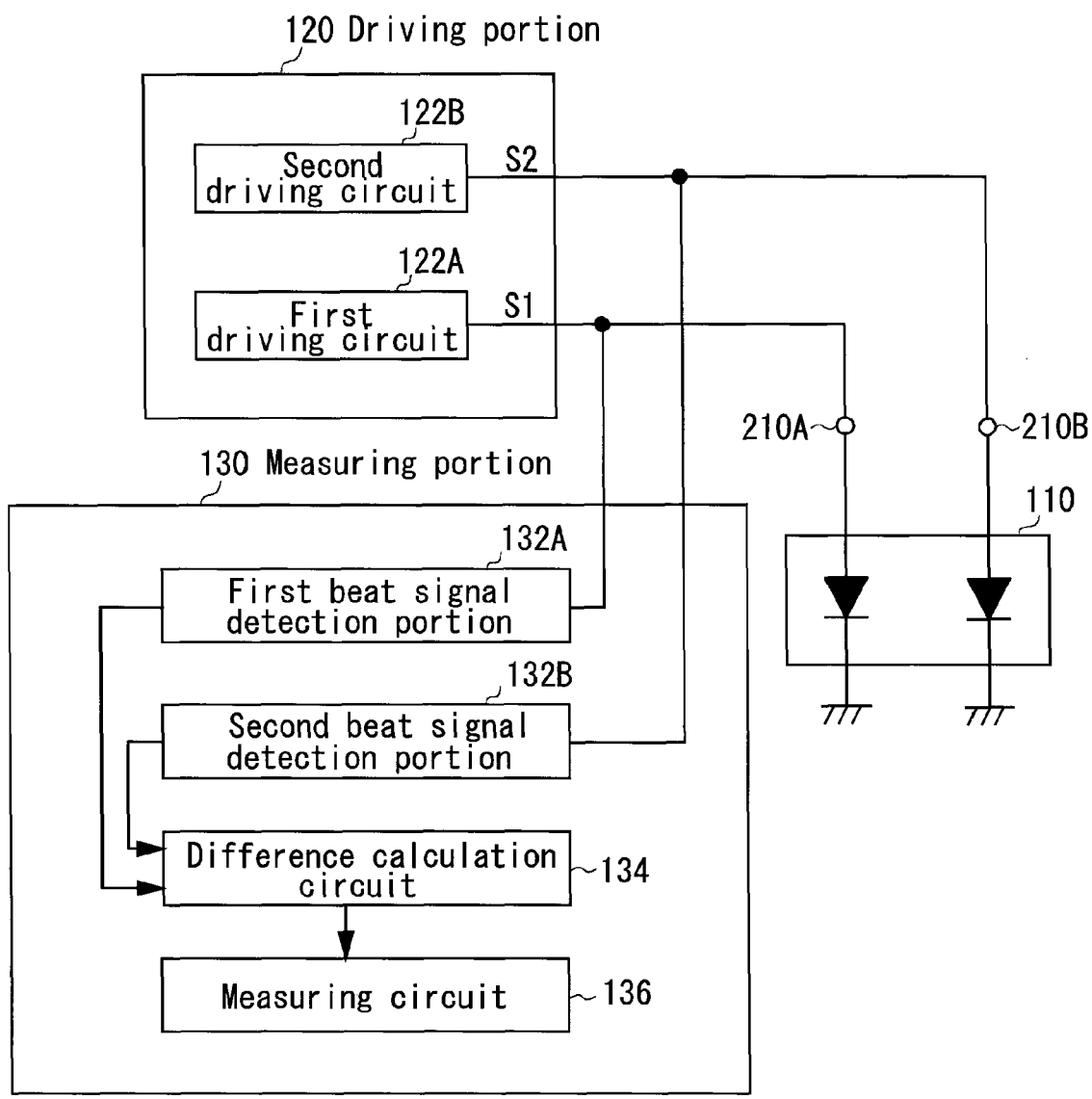
FIG. 4 illustrates an internal configuration of a driving portion and a measuring portion.

FIG. 4 is a block diagram illustrating an internal configuration of a driving portion and a measuring portion. The driving portion 120 may include a first driving circuit 122A that outputs a first driving signal S1 for driving the VCSEL of the post P1, and a second driving circuit 122B that outputs a second driving signal S2 for driving the VCSEL of the post P2. The first driving circuit 122A may provide the first driving signal S1 to the electrode pad 210A, and the second driving circuit 122B may provide the second driving signal S2 to the electrode pad 210B.

Figure 5:
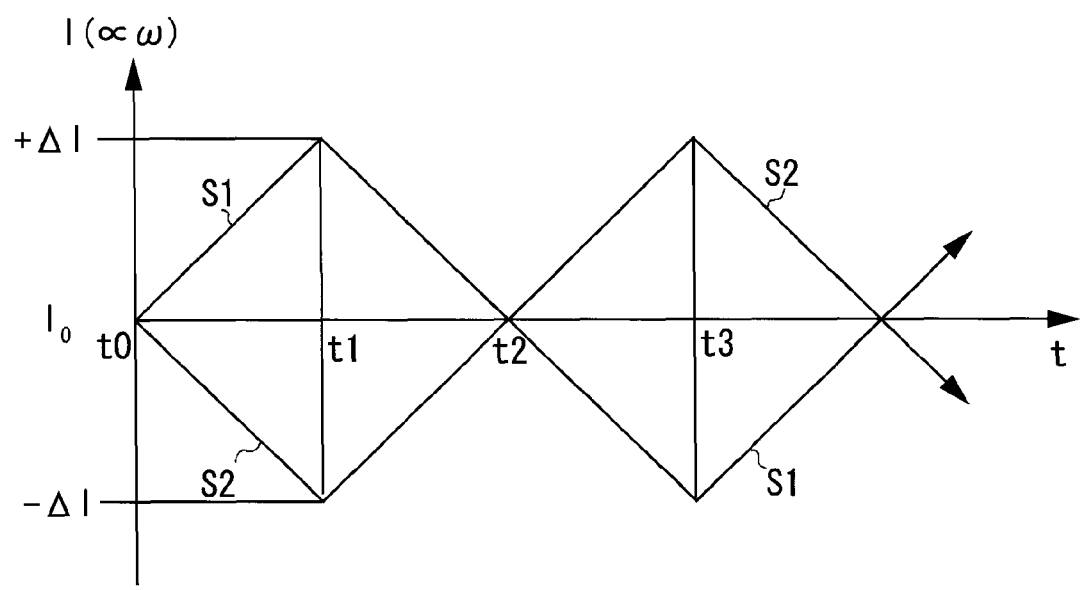
FIG. 5 illustrates waveforms of driving signals.

This example is characterized in that frequency modulation is performed for the laser light beams of the posts P1 and P2, wherein the modulation phases of the driving signals S1 and S2 are opposite each other. FIG. 5 is a diagram illustrating current waveforms of the first and second driving signals S1 and S2. The vertical axis shows the intensity of the laser light beams, and the horizontal axis shows time. If the reference oscillation intensity of the laser beam is $I_0$, then the first and second driving signals S1 and S2 are driving currents of a triangular wave in which the intensity changes between $+\Delta I$ and $-\Delta I$ are repeated, centering the reference oscillation intensity, and each of the first driving signal S1 and the second driving signal S2 is in a phase opposite to each other. In the example of FIG. 5, at time t0, the first and second driving signals S1 and S2 have the reference oscillation intensity $I_0$; at time t1, the first driving signal S1 has an intensity of $+\Delta I$ and the second driving signal S2 has an intensity of $-\Delta I$; at time t2, the first and second driving signals S1 and S2 have the reference oscillation intensity $I_0$; and at time t3, the first driving signal S1 has an intensity of $-\Delta I$ and the second driving signal S2 has an intensity of $+\Delta I$. For VCSELs, the driving current and the oscillation wavelength are in an approximately linear relation, and the larger the driving current becomes, the larger the oscillation wavelength becomes accordingly. Therefore, from the posts P1 and P2, laser light beams having opposite time-wise wavelength changes are emitted. The current waveform of the driving signals S1 and S2 is not limited to the shape as shown in FIG. 5, and may be a saw-tooth shape having a waveform different from this example.

As shown in FIG. 4, the measuring portion 130 may include a first beat signal detection portion 132A that detects a first beat signal whose light intensity is modulated due to the laser light emitted from the post P1 and its returned light, a second beat signal detection portion 132B that detects a second beat signal whose light intensity is modulated due to the laser light emitted from the post P2 and its returned light, a difference calculation circuit 134 that calculates a difference between the first and second beat signals, and a measuring circuit 136 that measures the state of the object to be measured based on the calculation result of the difference calculation circuit 134.

By modulating the light intensity of the semiconductor laser, the oscillation frequency can be varied. This modulation makes the oscillation frequency differ from the frequency of the returned light, and therefore modulation occurs in the laser medium, and a beat signal occurs in the light intensity. Larger the difference between the frequency of the returned light and the oscillation frequency means that the distance to the object to be measured is farther. Therefore, by analyzing the frequency of the beat signals, the distance between the laser and the object to be measured can be measured.

The first beat signal detection portion 132A shown in FIG. 4 may detect the first beat signal based on impedance changes in the driving signal S1 of the first VCSEL driving portion 122A. Specifically, when the laser light from the post P1 is emitted to an object to be measured, the returned light reflected or scattered from the object to be measured returns into the laser medium of the post P1, and the laser oscillation state thereof is modulated, and a beat signal is generated in the light intensity due to the difference between the frequencies of the laser light and the returned light. Similarly, the second beat signal detection portion 132B may detect a second beat signal based on the impedance changes in the driving signal S2 of the second VCSEL driving portion 112B. The first and second beat signals detected by the first and second beat signal detection portions 132A and 132B can be expressed in Equations (1) and (2).

$$I_1(t) = I_0 + \Delta I(t) + r\alpha I_0 \cos[(\Delta\omega + \Omega)t - k\Delta d] \quad (1)$$

$$I_2(t) = I_0 - \Delta I(t) + r\alpha I_0 \cos[(-\Delta\omega + \Omega)t - k\Delta d] \quad (2)$$

Where, if the intensity of the laser light emitted to the object to be measured is $I(=I_0+\Delta I)$, then $I_0$ is the reference oscillation intensity of the laser light, $\Delta I$ is the amount of modulation from the reference oscillation intensity $I_0$, r is the reflectivity of the object to be measured, $\alpha$ is the self-coupling efficiency of the laser light, $\Delta\omega$ is the difference between the oscillation frequency of the laser light emitted from the semiconductor laser device and the frequency of the reflected light, $\Omega$ is the amount of phase-shift due to the Doppler effect upon the reflection from the object to be measured, $\Delta d$ is the amount of displacement of the object to be measured, and k is the wave number vector of the reflected light.

The difference calculation circuit 134 may calculate a difference $|I_1-I_2|$ between the first beat signal and the second beat signal detected as described above. The calculated difference is given by Equation (3).

$$I_1 - I_2 = 2\Delta I + 2\alpha I_0 \sin[(\Omega t - k\Delta d)t] \sin(\Delta wt) \quad (3)$$

Figure 6:
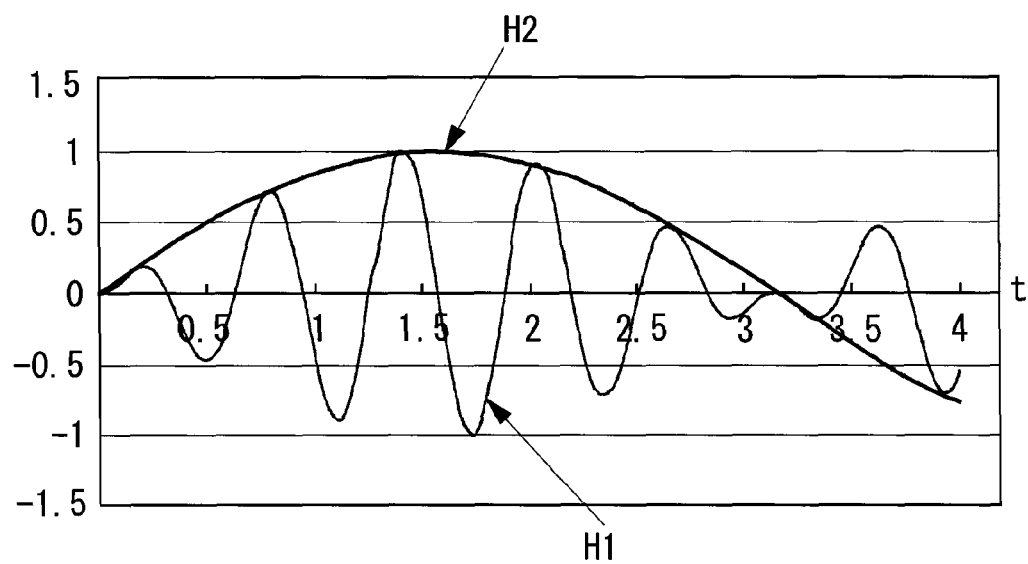
FIG. 6 illustrates a waveform of a first and a second beat signals and a differential signal.

FIG. 6 illustrates a waveform of a beat signal and a waveform of differences in beat signals. The first and second beat signals given by Equations (1) and (2) are signals that beat at a short period depicted as waveform H1. The signal given by Equation (3), which is the difference between the first and second beat signals, is a sinusoidal (sin) signal depicted as waveform H2.

The measuring circuit 136 is capable of measuring the velocity of hemoglobin or the blood flow amount, the object to be measured, from Equation (3) calculated by the difference calculation circuit 134. In other words, the variation of the object to be measured with respect to the oscillation at a modulation frequency $\Delta\Omega$ of the laser can be detected as a beat oscillation of $\sin(\Omega t - k\Delta d)$. In addition, it should be noted that the reflectivity r of the object to be measured is removed from Equation (3). This enables that, even if the reflectivity of the object to be measured, the reflectivity of hemoglobin in this case, varies, the state of the object to be measured is measured with a high SNR without being affected by the reflectivity.

Figure 7:
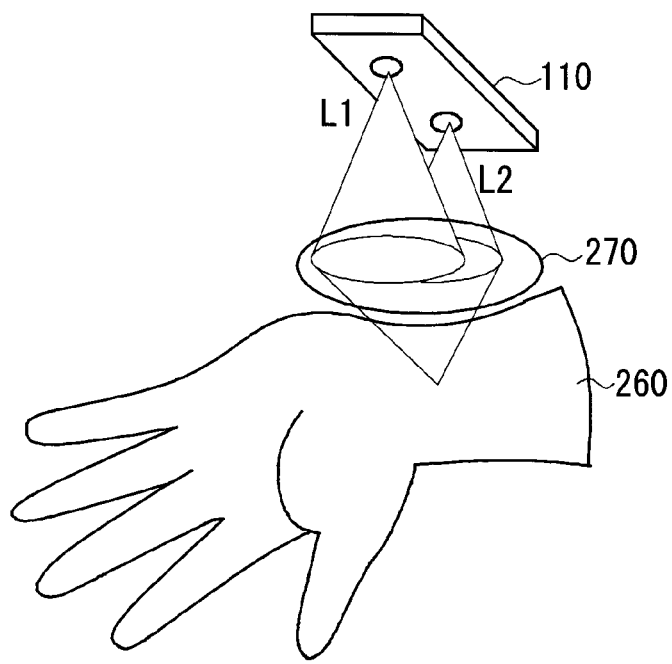
FIG. 7 illustrates an exemplary use of a blood flow sensor of an example.

FIG. 7 illustrates an exemplary use of a blood flow sensor of an example. The laser apparatus 110 of a blood flow sensor may be disposed near a human arm 260, and two laser light beams L1 and L2 are emitted from each of the light emitting portion of the laser apparatus 110 to the arm. The laser light beam having a wavelength of 850 nm may penetrate through the skin, and irradiate hemoglobin in the capillaries. A portion of reflected or scattered light from the surface of hemoglobin may contribute to the self-coupling effect as returned light, and the velocity of hemoglobin may be measured. Hemoglobin moves in the blood randomly, and the reflection surface thereof readily varies. In a measuring apparatus of a related art, variations in the reflectivity have been included as noises. However, in this example, the reflectivity r of hemoglobin in the measured Equation (3) is cancelled, and thus such noises are removed, thereby the velocity of hemoglobin, blood flow or the like can be accurately measured.

In a case where the signal of the object to be measured has an insufficient SNR, a lens 270 may be interposed between the laser apparatus 110 and the arm 260 to improve the efficiency in collecting the laser light beams L1 and L2 and the returned light. In addition, in the examples described above, the beat signal is detected from impedance changes in the driving signals S1 and S2 during laser oscillation. However, other than this example, a beat signal may be detected from an output signal of a light receiving device (photo detector) that monitors the laser oscillation state of a VCSEL (see FIG. 9 and FIG. 10.) The result measured by a blood flow sensor may be outputted from a display or a speaker, for example.

Figure 8:
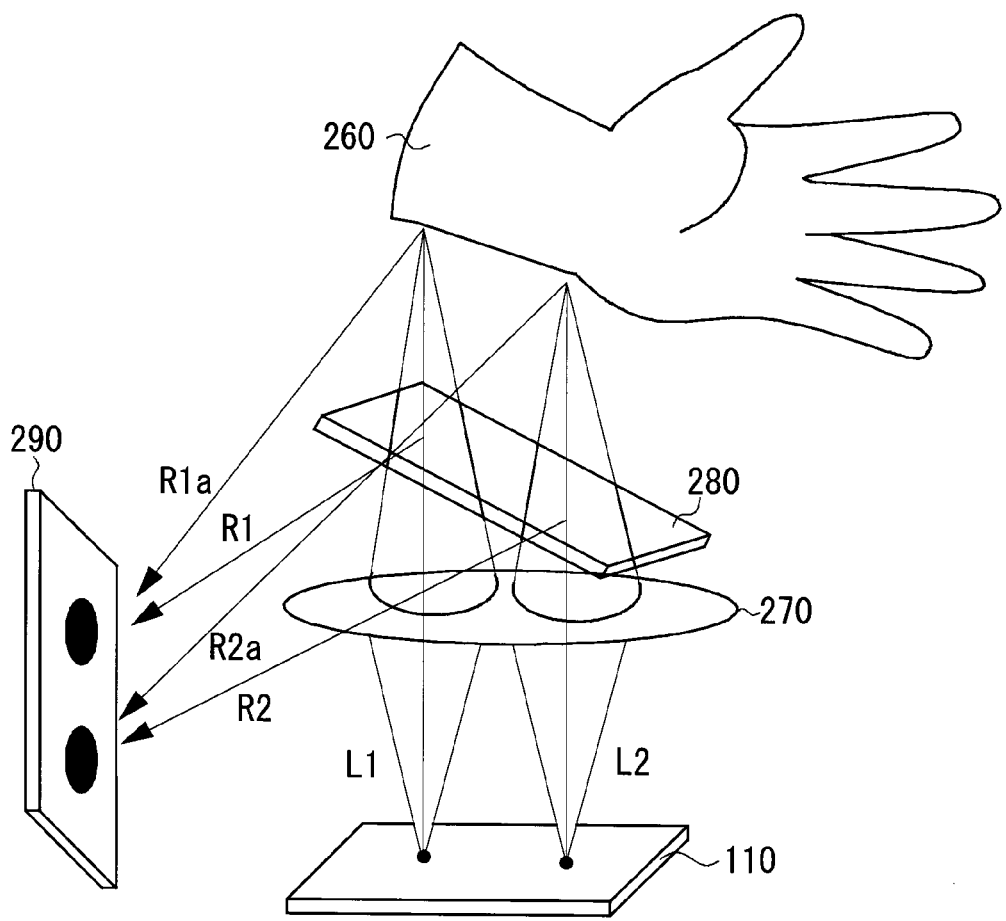
FIG. 8 illustrates a configuration of a blood flow sensor of a second example according to the present invention.

A second example of the present invention will be now described. According to the second example, as shown in FIG. 8, a blood flow sensor 100A may include a half mirror 280 and a detector 290 that detects an interference fringe. Similarly to the first example, the laser apparatus 110 may emit laser light beams L1 and L2 from the VCSELs modulated at opposite phases. The half mirror 280 may be disposed between the lens 270 and the object to be measured 260. The half mirror 280 allows a portion of the emitted laser light beams L1 and L2 to pass therethrough and irradiate the object to be measured 260, and allows a portion of the laser light beams L1 and L2 to reflect to the detector 290. With this configuration, reflected light beams R1 and R2 from the half mirror 280 and reflected light beams R1a and R1b from the object to be measured 260 may interfere with each other. By detecting variations in the interference fringes by the detector 290, a similar measurement to the measurement that uses the self-coupling effect of the first example may be done. The self-coupling effect of the first example causes interference in the laser and the interference is amplified and detected as a light intensity modulation; whereas, in the second example, a similar signal may be detected by an interferometer disposed out of the laser.

While exemplary embodiments of the present invention have been described in detail, the invention is not limited to these specific embodiments, and various modifications and changes can be made without departing from the inventive scope that is defined by the following claims.

What is claimed is:

1. A measuring apparatus comprising:
   a driving unit that outputs a first driving signal and a second driving signal having a phase opposite to that of the first driving signal;

a first semiconductor laser device, driven by the first driving signal, that emits a first laser light beam to an object to be measured;
a second semiconductor laser device, disposed in proximity to the first semiconductor laser device and driven by the second driving signal, that emits a second laser light beam to the object to be measured;
a first detection unit that detects a first electrical signal, the first electrical signal corresponding to the intensity of the first laser light beam modulated due to the self-coupling effect;
a second detection unit that detects a second electrical signal, the second electrical signal corresponding to the intensity of the second laser light beam modulated due to the self-coupling effect;
a calculation unit that calculates a difference between the first electrical signal and the second electrical signal; and
a measuring unit that measures a change in the state of the object to be measured based on the calculated difference;
wherein first and second detection units are configured to calculate the intensities of the first and second laser light beams modulated due to the self-coupling effect as expressed by Equations (1) and (2) respectively $$I_1(t)=I_0+\Delta I(t)+r\alpha I_0 \cos[(\Delta\omega+\Omega)t-k\Delta d] \quad (1)$$

$$I_2(t)=I_0-\Delta I(t)+r\alpha I_0 \cos[(-\Delta\omega+\Omega)t-k\Delta d] \quad (2)$$

where, if the intensity of the laser light emitted to the object to be measured is $I(=I_0+\Delta I)$, then $I_0$ is the reference oscillation intensity of the laser light beam, $\Delta I$ is the amount of modulation from the reference oscillation intensity $I_0$, r is the reflectivity of the object to be measured, $\alpha$ is the self-coupling efficiency of the laser light, $\Delta\omega$ is the difference between the oscillation frequency of the laser light beam emitted from the semiconductor laser device and the frequency of the reflected light, $\Omega$ is the amount of phase-shift due to the Doppler effect upon the reflection from the object, $\Delta d$ is the amount of displacement of the object to be measured, and k is the wave number vector of the reflected light; and
the calculation unit is configured to calculate the difference between the first electrical signal and the second electrical signal as expressed by Equation (3);

$$I_1-I_2=2\Delta I+2\alpha I_0 \sin[(\Omega t-k\Delta d)t]\sin(\Delta wt) \quad (3)$$

where the reference oscillation intensity $I_0 \gg$ the amount of modulation $\Delta I$.

2. The measuring apparatus according to claim 1, wherein the first and second semiconductor laser devices are surface emitting semiconductor laser devices formed spaced apart from each other on a common substrate.

3. The measuring apparatus according to claim 1, wherein each of the first and second driving signals is a driving current having a saw-tooth wave.

4. The measuring apparatus according to claim 1, wherein the first and second detection units detect the first and second electrical signals based on an impedance change in the first and second driving signals of the driving unit.

5. The measuring apparatus according to claim 1, further comprising a first and a second light receiving devices that receive a portion of the first and second laser light beams emitted from the first and second semiconductor laser devices, wherein
the first and second detection units detect the first and second electrical signals based on a first and a second light receiving signals outputted from the first and second light receiving devices.

6. The measuring apparatus according to claim 1, further comprising a lens between the first and second semiconductor laser devices and the object to be measured.

7. The measuring apparatus according to claim 1, wherein the measuring unit measures the velocity of hemoglobin in the blood.

* * * * *